US009815535B2

(12) United States Patent
de Rivero

(10) Patent No.: US 9,815,535 B2
(45) Date of Patent: Nov. 14, 2017

(54) AIR BUBBLE

(71) Applicant: Felipe Kelly de Rivero, Orlando, FL (US)

(72) Inventor: Felipe Kelly de Rivero, Orlando, FL (US)

( * ) Notice: Subject to any disclaimer, the term of this patent is extended or adjusted under 35 U.S.C. 154(b) by 162 days.

(21) Appl. No.: 14/986,038

(22) Filed: Dec. 31, 2015

(65) Prior Publication Data

US 2016/0167753 A1 Jun. 16, 2016

Related U.S. Application Data

(63) Continuation-in-part of application No. 14/199,413, filed on Mar. 6, 2014, now abandoned.

(51) Int. Cl.

| | |
|---|---|
| ***A61M 16/00*** | (2006.01) |
| ***B63C 11/22*** | (2006.01) |
| ***A62B 7/12*** | (2006.01) |
| ***A62B 9/04*** | (2006.01) |
| *A62B 9/06* | (2006.01) |

(52) U.S. Cl.

CPC ................ *B63C 11/22* (2013.01); *A62B 7/12* (2013.01); *A62B 9/04* (2013.01); *A62B 9/06* (2013.01)

(58) Field of Classification Search

CPC ........ A61M 16/0078; A62B 7/12; A62B 9/04; A62B 25/00; A62B 33/00; B63C 11/22

See application file for complete search history.

(56) References Cited

U.S. PATENT DOCUMENTS

| | | | | |
|---|---|---|---|---|
| 2,696,211 A * | 12/1954 | O'Gatty | A61M 15/0028 | 128/205.21 |
| 3,656,196 A * | 4/1972 | O'Neill | B63C 11/30 | 128/205.13 |
| 4,183,422 A * | 1/1980 | Williams | B63C 11/26 | 128/201.19 |
| 4,821,712 A * | 4/1989 | Gossett | A62B 7/02 | 128/204.26 |
| 5,060,833 A * | 10/1991 | Edison | A45F 5/00 | 215/388 |
| 5,490,501 A * | 2/1996 | Crowley | A63B 29/021 | 128/200.24 |
| 5,820,432 A * | 10/1998 | Wright | B63C 9/1255 | 441/119 |
| 6,405,728 B1 * | 6/2002 | Van Hall | A62B 25/00 | 128/202.13 |
| 2001/0027787 A1 * | 10/2001 | Reed, III | A62B 7/12 | 128/200.24 |
| 2006/0005831 A1 * | 1/2006 | Stewart | B63C 9/1255 | 128/201.27 |
| 2015/0250965 A1 * | 9/2015 | De Rivero | A62B 7/12 | 128/205.13 |

FOREIGN PATENT DOCUMENTS

NL 1030574 C2 * 6/2007

* cited by examiner

*Primary Examiner* — Kristen Matter

(57) ABSTRACT

An apparatus that stores air for underwater use in an emergency. The device includes an air and water impermeable reservoir having reinforcing ribs each with a hole to allow air flow within the reservoir. The reservoir is filled with air through a mouthpiece via an air pump. The mouthpiece is fluidly connected to the reservoir with an air transfer channel to allow a user to take several breaths of air when underwater.

3 Claims, 2 Drawing Sheets

AIR BUBBLE

CROSS-REFERENCE TO RELATED APPLICATIONS

This application is a Continuation-in-part (CIP) of U.S. patent application Ser. No. 14/199,413, filed on Mar. 6, 2014, now abandoned.

STATEMENT REGARDING FEDERALLY SPONSORED RESEARCH OR DEVELOPMENT

Not Applicable

BACKGROUND OF THE INVENTION

Air Bubble allows for several air breaths under water, depending on the size of the Air Bubble and the user's lung capacity.

BRIEF SUMMARY OF THE INVENTION

Air Bubble is an apparatus that consists of an air- and water-impermeable reservoir inflated with air via an external air pump, and the air is stored so that a user can take several breaths of air under water. The air- and water-impermeable reservoir is inflated by an external air pump via the mouthpiece. The mouthpiece is connected to an air channel, which is connected to the air- and water-impermeable reservoir. Inside the air- and water-impermeable reservoir are reinforcing ribs with evenly spaced holes in each rib to allow air flow within the reservoir. The reinforcing ribs also serve to shape the Air Bubble to the user's body, as well as add an impact-resistant capability. Air is released from the air- and water-impermeable reservoir through the air-transfer channel to the user when pressure is applied to the mouthpiece's exterior walls by the user's mouth. The air- and water-impermeable reservoir can be reinflated with an air pump for repeated use.

DETAILED DESCRIPTION OF THE INVENTION

Figure 1:
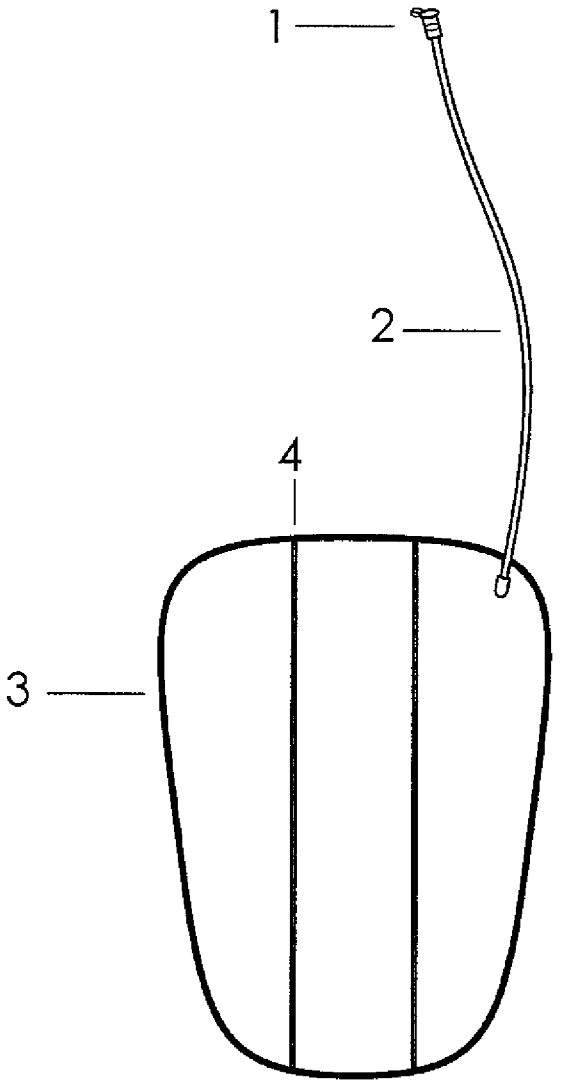
FIG. 1 depicts a top view of the Air Bubble and its interior and exterior components.
Figure 2:
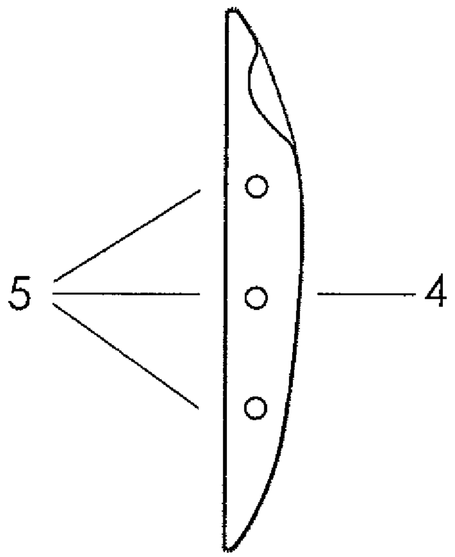
FIG. 2 depicts a cut-through-section view of the air- and water-impermeable reservoir.

In order for the advantages of the invention to be readily understood, a more particular description of the invention briefly described above will be rendered by reference to specific embodiments that are illustrated in the drawings. Understanding that these drawings depict only typical embodiments of the invention and are not therefore to be considered to be limiting of its scope, the invention will be described and explained with additional specificity and detail through the use of the accompanying drawings, in which the reference characters refer to the following elements:

1. Mouthpiece
2. Air-Transfer Channel
3. Air- and Water-Impermeable Reservoir
4. Reinforcing Ribs
5. Evenly-Spaced Holes The mouthpiece (1) is made of thermoplastic polyurethane (TPU), which is a commercially available material. The mouthpiece (1) will release air stored in the reservoir when pressure is applied to the exterior walls of the mouthpiece (1) by a user's mouth. The mouthpiece (1) is in fluid communication with the air- and water-impermeable reservoir (3) via an air transfer channel (2) so that the mouthpiece (1) releases stored air through the air transfer channel (2) upon applied pressure to the mouthpiece's exterior walls via the user's mouth.

The air transfer channel (2) is made of TPU and is coupled to the mouthpiece (1) and the air- and water-impermeable reservoir (3), allowing air to pass from the reservoir (3) to the mouthpiece (1).

The air- and water-impermeable reservoir (3) is made of TPU and stores air when filled with a commercially available air pump (not shown). The air- and water-impermeable reservoir may be located within a backpack, wetsuit, or floatation device (not shown).

The reinforcing ribs (4) are made of TPU and are impact-resistant. The ribs each have evenly spaced holes (5) that allow airflow within the air- and water-impermeable reservoir (3). The reinforcing ribs (4) also shape the air- and water-impermeable reservoir (3) to the user's body, and add an impact-resistant capability to the Air Bubble. The three evenly-spaced holes (5) allow air flow within the air- and water-impermeable reservoir (3).

The invention claimed is:

1. An apparatus to store air for underwater use, the apparatus comprising:

an air and water impermeable reservoir comprising reinforcing ribs, the reinforcing ribs each comprising a hole to allow air flow within the reservoir;

a mouthpiece for releasing air stored within the reservoir in response to pressure being applied to exterior walls of the mouthpiece;

an air transfer channel providing fluid communication between the reservoir and the mouthpiece;

wherein the reservoir is configured to be filled with air through the mouthpiece via an air pump so that a user can take several breaths of air from the reservoir when the user is underwater.

2. The apparatus of claim 1, wherein the reservoir is located within a backpack, wetsuit, or floatation device.

3. The apparatus of claim 1, wherein the hole in each reinforcing rib is one of three evenly spaced holes in each reinforcing rib.

* * * * *